(12) United States Patent
Reich et al.

(10) Patent No.: US 6,294,159 B1
(45) Date of Patent: *Sep. 25, 2001

(54) VOLUMIZING HAIR CARE COMPOSITIONS

(75) Inventors: Charles Reich, Highland Park, NJ (US); Elizabeth Paradi, Evanston, IL (US); Janine Chupa; Cheryl L. Kozubal, both of Somerset, NJ (US); Dean Terng-Tzong Su, Princeton Junction, NJ (US)

(73) Assignee: Colgate Palmolive Company, NY, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/405,994

(22) Filed: Sep. 27, 1999

Related U.S. Application Data

(63) Continuation-in-part of application No. 09/169,656, filed on Oct. 9, 1998, now abandoned.

(51) Int. Cl.⁷ ..................................................... A61K 7/06
(52) U.S. Cl. ................. 424/70.12; 424/70.1; 424/70.11; 510/119; 510/122; 528/39; 556/445
(58) Field of Search ............................ 424/401, 47, 70.1, 424/70.11, 70.12; 510/119, 122; 528/39; 556/445

(56) References Cited

U.S. PATENT DOCUMENTS

| | | |
|---|---|---|
| 2,528,378 | 10/1950 | Mannheimer et al. . |
| 3,577,517 | 5/1971 | Kobot . |
| 3,772,247 | 11/1973 | Flannigan . |
| 3,907,984 | 9/1975 | Calvert et al. . |
| 4,012,501 | 3/1977 | Farber . |
| 4,223,009 | 9/1980 | Chakrabarti . |
| 4,283,384 | 8/1981 | Jacquet et al. . |
| 4,741,855 | 5/1988 | Grote et al. . |
| 4,774,310 | 9/1988 | Butler . |
| 4,902,499 | 2/1990 | Bolish, Jr. et al. . |
| 4,963,348 | 10/1990 | Bolich, Jr. et al. . |
| 5,015,415 | 5/1991 | Goze et al. . |
| 5,120,531 | 6/1992 | Wells et al. . |
| 5,585,094 | 12/1996 | Villamarin . |
| 5,817,302 | * 10/1998 | Berthiaume et al. . |

FOREIGN PATENT DOCUMENTS

| | | |
|---|---|---|
| 0240350 | 4/1987 | (EP) . |
| 2297757 | 2/1996 | (GB) . |
| 9506057 | 8/1993 | (WO) . |
| 9638120 | 6/1995 | (WO) . |

\* cited by examiner

Primary Examiner—Thurman K. Page
Assistant Examiner—Brian K. Seidleck
(74) Attorney, Agent, or Firm—Rosemary M. Miano

(57) ABSTRACT

This invention relates to an improved formulation hair volumizers which comprise: (a) from 0.01–15 percent by weight (based on the total weight of the composition) of a selected liquid MQ resin having an M:Q ratio of 0.5–1.5 and a medium viscosity in the range of $1.0 \times 10^3 – 1 \times 10^6$ centipoise; and (b) from 85–99.99 percent by weight (based on the total weight of the composition) of a hair care carrier (also called a vehicle). The compositions of this invention provide hair with increased volume without significant stiffness or stickiness and may be made in the form of a shampoo, conditioner, combination shampoo/conditioner, sprays, liquid rinses, gels or mousses.

20 Claims, No Drawings

VOLUMIZING HAIR CARE COMPOSITIONS

This application is a CIP of U.S. Ser. No. 09/169,656 filed Oct. 9, 1998 now abandoned

FIELD OF THE INVENTION

This invention relates to an improved formulation for treating hair. In particular, the compositions of this invention incorporate a selected type of siloxysilicate polymer (known as MQ silicone resins) in hair care formulations that can be used as hair volumizers. This case is related to a co-pending case filed on the same day as this case as U.S. Ser. No. 09/406,543 and owned by the same company as this case.

BACKGROUND OF THE INVENTION

The search for improved hair care products is a continual one. Since hair types vary, so do the types of products that are useful in working with different types of hair. One such product category desired by people to create a fuller appearance for their hair is known as hair volumizers. Previous attempts at adding volume to hair have involved the use of fixative-based sprays, gels or mousses to enhance styling and create volume. These products work by gluing hair together in a fixed architecture with increased volume. Such products often have the disadvantage of causing hair to be stiff or excessively sticky and do not, in general, allow the user to restyle the hair without washing out the product and reapplying it. The adhesive character of these volumizers can create difficulty in restyling. Additionally, such fixative-based products may initially cause a volumizing effect, but continued use of these products over time can result in build up on the hair resulting in loss of hair volume. The problem is magnified for people with fine hair since that type of hair is especially sensitive to being weighed down by deposits from hair care products.

The consumer wants volumizing products which are not permanent wave products, or fixative-based hair sprays or styling gels. The consumer does want a volumizing product which can add volume to otherwise flat or thin hair while maintaining some ability to restyle hair. Thus, hair volumizers as used in this context do not create a permanent architecture for the hair but allow the hair to be restyled and revolumized.

One example of a retention aid for hair styling is PCT Patent Application Publication Number WO 95/06057 to Torgerson et al. This reference describes silicone grafted thermoplastic elastomeric copolymers and hair and skin care compositions containing the same. These copolymers are useful in hair spray and mousse compositions. The copolymers described in this reference are water or alcohol soluble or dispersible thermoplastic elastomeric copolymers having a backbone and two or more hydrophilic polymeric side chains and one or more polysiloxane side chains, wherein the copolymer comprises:

(a) 20–89.9% monomer units copolymerizable with (b) and (c);
(b) 10–60% hydrophilic macromonomer units having a polymeric portion and a moiety copolymerizable with (a) and (c);
(c) 0.1–20% polysiloxane macromonomer units having a polymeric portion and a moiety copolymerizable with (a) and (b).

U.S. Pat. No. 4,902,499 to Bolich et al teaches hair care compositions which give both improved style retention and hair conditioning. The compositions comprise 0.01–10% of a rigid silicone polymer and a volatile carrier. Suitable polymers include filler reinforced polydimethyl siloxane gums, cross-linked siloxanes, organic substituted siloxane gums, resin reinforced siloxanes and cross-linked siloxane polymers.

European Patent Application EP 0 0240 350 B1 to Snyder et al claims the use of compositions having style retention and hair conditioning properties wherein the composition comprises (a) a rigid silicone polymer having a complex viscosity of at least $1\times10^6$ Pascal seconds ($1\times10^7$ poise) selected from the group consisting of organic substituted siloxane gums, silicone elastomers, filler reinforced polydimethyl siloxane gums, resin reinforced siloxanes and cross-linked siloxane polymers; and (b) a volatile carrier selected from water, straight chain or branched C10–C16 volatile hydrocarbons, and volatile silicones having a boiling point in the range of 99–260 degrees C, wherein if water is the sole carrier, from 0.05–50% by weight of a surfactant is also present and wherein is excluded the use of a silicone polymer in the manufacture of an aqueous aerosol hair styling mousse composition wherein the silicone polymer is in the form of an emulsion comprising an anionically stabilized hydroxylated polyorganosiloxane.

Other attempts have included the creation of hair thickeners. PCT Patent Application Publication Number WO 96/38120 to Grossman describes a hair thickener and conditioning gelatin composition for topical application to the hair. A formulation comprising an aqueous gelatin solution, a water-soluble film-forming polymer, and an acid neutralizing agent to maintain the pH of the composition in the range of 6.0–9.5 is disclosed. The types of water-soluble, film-forming polymers suitable for us with this composition include polyvinyl pyrrolidone (PVP), polyvinyl acetate, partially hydrolyzed polyvinyl acetate, copolymers of PVP and vinyl acetate, polyvinyl alcohol, acrylate-acrylamide copolymers, acrylate-PVP copolymers and the like, wherein the polymers have a number average molecular weight ranging between 5,000–10,000 daltons.

Siloxane resins consisting of triorganosiloxane units and silicon dioxide units are known, commercially available materials and are employed in the formulation of various products including adhesives, anti-foaming agents as well as personal care products; however, it is not believed that these compounds have been used commercially in hair care products of the type described here. Such resins are sometimes referred to as "MQ resins" because of the presence of the monovalent (M) siloxane units and the quadrivalent or tetravalent (Q) silicon dioxide units.

In view of the reactivity of the silyl hydride group, it is sometimes desired to include such groups in MQ type resins. Siloxane resins composed of silicon dioxide units and units of the general formula $H^1R^2SiO_{1/2}$, where each of $R^1$ and $R^2$ may be the same or different and each is selected from hydrogen, a monovalent hydrocarbon and a monovalent halohydrocarbon are frequently used because of the high reactivity of the silyl hydride functionality therein. Such resins have been used for organopolysiloxane elastomers. As precursors to other synthetic silicones, it is frequently desirable that these resins contain a limited number of silyl groups. U.S. Pat. No. 3,772,247 discloses organopolysiloxane resins consisting of $R^3R^4R^5SiO_{1/2}$ units, $SiO_2$ units and units of the type $HR^3SiO$ and/or $HSiO_{3/2}$ in which each of $R^3$, $R^4$, and $R^5$ are independently selected from the group consisting of alkyl, aryl, alkaryl, alkenyl, cycloalkyl and cycloalkenyl groups. While such resins possess silyl hydride groups, they possess a significant and measurable level of divalent or trivalent organosiloxyl groups.

U.S. Pat. No. 4,774,310 to Butler discloses MQ resins consisting of $R^3R^4R^5SiO_{1/2}$ units and $SiO_2$ units where $R^3$, $R^4$, and $R^5$ are independently selecte from the group consisting of alkyl, aryl, alkaryl, alkenyl, cycloalkyl and cycloalkenyl groups. The MQ resins of this reference are further reacted with disiloxanes using acidic catalysis to product MQ type siloxane resins where the M:Q ratio is in the range of 0.4:1to 1:1, and where the fraction of hydride stopped units of the general formula $H_aR''_{3-a}SiO_{1/2}$, where $R''$ is selected from the same group as defined for $R^3$, $R^4$, and $R^5$ is in the range of 0.1–30 percent of the total number of M units present.

British Patent 2,297,757 to Berthiaume et al describes low viscosity organofunctionalized siloxysilicates which are of the "MQ" type and which are stated as being useful as cosmetic and personal care products. These functionalized MQ silicone resins have the general formula:

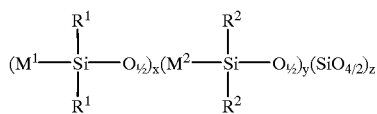

where both $R^1$ and $R^2$ may be either a phenyl group or a C1–C12 alkyl group and both $M^1$ and $M^2$ are independently selected from the group consisting of phenyl, phenethyl, polyether, hydrogen and C1–C23 alkyl group (which may also include halogen substituted hydrocarbon radicals) and wherein x, y and z satisfy the following relationship: $0.5 \leq (x+y)/z \leq 4.0$ and one of x and y may be zero.

U.S. Pat. No. 5,585,094 to Villamarin discloses a method for semi-permanently conditioning the hair wherein a low viscosity oil-in water emulsion of a mixture of two polysiloxane polymers is applied (one being a hydroxy terminated dimethyl polysiloxane and the other being a methyl hydrogen polysiloxane) at an acid pH and in an unreacted state. Preferably heat is applied to crosslink the polymers.

U.S. Pat. No. 4,963,348 to Bolich et al describes styling agents and compositions comprising adhesive copolymers with a volatile diluent to provide hair styling and hold.

There still remains a need, however, to provide compositions suitable for use as hair volumizers which do not leave the hair stiff or excessively sticky.

Thus, it is an object of the present invention to provide volumizing compositions that do not rely on sticking hair fibers together to achieve volume increases. In particular, it is an important object of this invention to provide a hair volumizer which is capable of giving volume to hair without substantial adhesion between the hair fibers. It is a further object of the invention to provide a hair volumizer which allows the hair to be manipulated and re-volumized between washings. It is also an object of the present invention to provide compositions suitable for use as hair volumizers which are useful to increase hair volume by a substantial amount. It is yet another object of the present invention to provide compositions suitable for use as hair volumizers which use MQ resins and which allow the hair to withstand compression of the hair network. These and other objects of the invention will become apparent from the following description.

SUMMARY OF THE INVENTION

The compositions of this invention are hair volumizers which comprise:

(a) from 0.01–15 percent by weight (based on the total weight of the composition) of a selected liquid MQ resin having an M:Q ratio of 0.5–1.5 and a medium viscosity in the range of $1.0 \times 10^3 – 1 \times 10^6$ centipoise ("cps" or "cP") (for example, 0.1–10% by weight, more particularly 0.1–7.0% and, most particularly, 0.1–4%); and (b) from 85–99.99 percent by weight (based on the total weight of the composition) of a hair care carrier (also called a vehicle).

The compositions of this invention provide hair with increased volume without significant stiffness, or excessive stickiness or build-up of product on the hair which would contribute to loss of volume. The compositions of this invention may be made in the form of a shampoo, conditioner, combination shampoo-conditioner (so-called 2-in-1products), sprays, liquid rinses, gels or mousses.

DETAILED DESCRIPTION OF THE INVENTION

The compositions of this invention are made with one or more selected liquid MQ resins having an M:Q ratio of 0.5–1.5 (also referred to as the x+y/z ratio (for Formula IA) or x'/z' ratio if the x segment and the y segment are the same, as in Formula IB) and a viscosity in the range of $1.0 \times 10^3 – 1 \times 10^6$ centipoise ("cps" or "cP") (or $1.0 – 1 \times 10^3$ Pa-sec); particularly $1.5 \times 10^3 – 1 \times 10^6$, more particularly 1000–100,000, even more particularly 1000–50,000 cps, and still more particularly 1000–20,000 cps, such as 2,000–14,000 cps, with a particular example being 3,000–12,000 cps. While it is possible to use MQ resins with higher viscosities (such as 50,000–100,000 cps), it is more convenient to use the lower viscosities.

The MQ resins suitable for use with this invention may be represented by Formula IA:

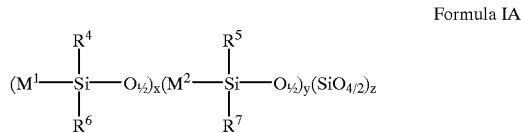

Formula IA wherein $R^4$, $R^5$, $R^6$, and $R^7$ are each independently selected from the group consisting of phenyl and C1–C12 branched and unbranched hydrocarbons, particularly C1–C12 branched and unbranched alkyl, more particularly branched and unbranched C1–C5 alkyl and especially methyl; $M^1$ and $M^2$ are each independently from the group consisting of (a) hydrogen,
(b) phenyl,
(c) phenethyl,
(d) a polyether of Formula II:

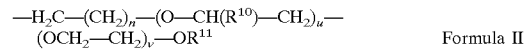

Formula II where n is a number from 1–20 and the —($CH_2$)— chain may optionally contain 1 or 2 unsaturations; u and v are integers each independently selected from 0–20, provided that $u+v \leq 1$; $R^{10}$ is selected from C1–C20 alkyl; and $R^{11}$ is selected from the group consisting of H, —$CH_3$ and —C(O)$CH_3$); and (e) C1–C24 branched and unbranched hydrocarbons optionally substituted by a halogen substituted C1–C3 hydrocarbon radical, with a particular value for $R^2$ being C1–C24 alkyl, especially methyl; and wherein (x+y)/z is a number in the range of 0.5 and 1.5, and is preferably equal to 1; and the values for $R^4$, $R^5$, $R^6$, $R^7$, x, y, z, $M^1$ and $M^2$ are selected to so that the MQ resin is a liquid having a viscosity of $1.0 \times 10^3 – 1 \times 10^3$ centipoise, such as $1.5 \times 10^3 – 1 \times 10^6$ centipoise.

A particular type of MQ resin of Formula IA when x and y are the same may be represented by Formula IB:

Formula IB

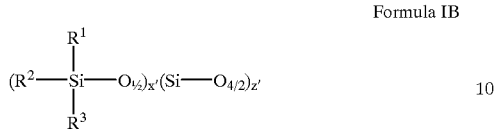

wherein $R^1$ and $R^3$ are each independently selected from the same group as defined for $R^4$, $R^5$, R6 and $R^7$ of Formula IA; $R^2$ is selected from the same group as described for $M^1$ and $M^2$; and x'/z' is a value between 0.5 and 1.5.

A particular MQ useful in the invention is a liquid trimethylsiloxysilicate polymer, especially with an M:Q ratio of 1(for example a resin obtained from General Electric Company, Waterford, N.Y. as "MQ-A").

The MQ resins useful in this invention are to be distinguished from other types of MQ resins which do not have all of the desirable properties of the invention. As described in more detail below, it has been found that low viscosity liquid MQ resins with an M:Q ratio of 2 do not give significant volume and do not exhibit significant adhesive character on the hair; solid MQ resins with an M:Q ratio of 2 do not give significant volume and also do not exhibit significant adhesive character on the hair; and solid MQ resins with an M:Q ratio of 0.7–1.0 give volume but do exhibit significant adhesive character on the hair.

The vehicle in which the MQ resin is present is a member selected from the group consisting of sprays, rinses, shampoos, conditioners and "2-in-1" conditioning shampoos. In particular, these products may be formed with a volatile carrier (that is, a carrier having a measurable vapor pressure) such as volatile silicones, C2–C3 alcohols, isopropyl myristate and water, and mixtures of the foregoing, provided that if water is the only carrier at least one surfactant is also used. One class of preferred carriers are volatile silicones having a boiling point between 99 degrees C and 260 degrees C. The silicones may be either linear or cyclic polydimethyl siloxanes where the cyclic polydimethyl siloxanes contain from 3 to about 7 silicon atoms, most preferably 5. These volatile silicones may be used alone or in combination with other volatile carriers. A particular volatile silicone is cyclomethicone (especially a D5 cyclomethicone).

If water is the sole carrier, a surfactant (from the group described below) in an amount of 0.1–50% by weight of the total composition is also present.

Shampoos may be used as carriers to which the selected MQ resin is added. Suitable shampoos include both regular and conditioning shampoos. Particular shampoos include those formulated with a surfactant, a stabilizer and the selected liquid MQ resin as described above. Other optional ingredients such as thickeners, preservatives, fragrance, opacifiers, foam modifiers, etc. can be included in such formulations as noted below.

Suitable surfactants include:

(a) anionics as described in U.S. Pat. No. 4,902,499 to Bolich et al and U.S. Pat. No. 4,963,348 to Bolich et al both of which are incorporated by reference herein such as
  (i) alkyl and alkyl ether sulfates of formula $R^{20}OSO_3M$ and $R_{20}O(C_2H_4O)_wSO_3M$, wherein $R^{20}$ is alkyl or alkenyl of 10–20 carbon atoms, w is a number from 1 to 10, and M is a water-soluble cation such as ammonium, sodium, potassium and triethanolamine;
  (ii) reaction products of fatty acids (for example, those derived from coconut oil) esterified with isethionic acid and neutralized with sodium hydroxide;
  (iii) succinamates (for example disodium N-octadecylsulfosuccinates, tetrasodium N-(1,2-dicarboxyethyl)-N-octadecylsulfosuccinamate, diamyl ester of sodium sulfosuccicinic acid, dihexyl ester of sodium sulfosuccinic acid, and dioctyl esters of sodium sulfosuccinic acid; and
  (iv) olefin sulfonates having 12 to 24 carbon atoms;

(b) amphoterics as described in U.S. Pat. No. 4,902,499 to Bolich et al and incorporated by reference herein such as
  (i) derivatives of aliphatic secondary and tertiary amines in which the aliphatic radical can be straight chain or branched and wherein one of the aliphatic substituents contains from 8 to 18 carbon atoms and one contains an anionic water solubilizing group (for example, carboxy, sulfonate, sulfate, phosphate, or phosphonate) with examples of such compounds including sodium 3-dodecyl-aminopropionate, sodium 3-dodecylaminopropane sulfonate, N-alkyltaurines, N-higher alkyl aspartic acids (for example products sold under the name "MIRANOL" as described in U.S. Pat. No. 2,528,378);
  (ii) zwitterionic surfactants (broadly exemplified as derivatives of aliphatic quaternary ammonium, phosphonium, and sulfonium compounds, in which the aliphatic radicals can be straight chain or branched, and wherein one of the aliphatic substitutents contains from 8 to 18 carbon atoms and one contains an anionic water-solubilizing group (for example, carboxy, sulfonate, sulfate, phosphate, or phosphonate);
  (iii) betaines, for example, high alkyl betaines such as cocodimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxyethyl)carboxymethyl betaine, stearyl bis-(2-hydroxy-propyl) carboxymethyl betaine, oleyl dimethyl-gamma-carboxypropyl betaine, lauryl bis-(2-hydroxypropyl) alpha-carboxyethyl betaine, and cocamidopropyl betaine.

(c) nonionic surfactants including those selected from the group described in U.S. Pat. No. 4,741,855 to Grote et all and incorporated by reference herein; these are
  (i) polyethylene oxide condensates of alkyl phenols wherein the alkyl portion of the alkyl phenol has 6–12 carbons and may be straight chain or branched and the ethylene oxide portion is present in an amount of 10–60 moles of ethylene oxide per mole of alkyl phenol;
  (ii) condensation products of ethylene oxide with a product resulting from the reaction of propylene oxide and ethylene diamine varied according to the hydrophobic/hydrophilic balance desired (for example, compounds containing from 40–80% polyoxyethylene by weight and having a molecular weight of from 5,000–11,000 resulting from the reaction of ethylene oxide groups with a hydrophobic base constituted of the reaction product of eth ylene diamine and excess propylene oxide, wherein the base has a molecular weight of 2500–3,000);

(iii) condensation products of C8–18 straight or branched chain aliphatic alcohols with ethylene oxide (for example, coconut alcohol ethylene oxide condensate with 10–30 moles of ethylene oxide per mole of coconut alcohol wherein the coconut fraction has 10–14 carbon atoms);.

(iv) long chain tertiary amine oxides of formula ($R^{30}$) ($R^{31}$)($R^{32}$)—N→O, wherein $R^{30}$ is an C8–18 alkyl, alkenyl or monohydroxy alkyls; which has from 0–10 ethylene moieties and from 0–1 glyceryl moiety; and $R^{31}$ and $R^{32}$ may be the same or different and are each independently selected from the group consisting of C1–3 alkyls with 0–1 hydroxy group. The arrow in the structure is a conventional representation of a semipolar bond. Examples of suitable long chain tertiary amine oxides include cocamidopropylamine oxide and lauramine oxide.

(v) long chain tertiary phosphine oxides of Formula: $R^{20}R^{21}R^{22}P→O$ where $R_{20}$ contains a C8–18 alkyl, alkenyl or monohydroxyalkyl radical; 0–10 ethylene oxide moieties and 0–1glyceryl moiety; and $R^{21}$ and $R^{22}$ are each independently C1–3 alkyl or monhydroxyalkyl. The arrow in the formula is a conventional representation of a semipolar bond.

(vi) long chain dialkyl sulfoxides containing one short chain alkyl or hydroxy alkyl radical of 1–3 carbons (particularly methyl) and one long hydrophobic chain having a C8–20 alkyl, alkenyl, hydroxy alkyl or keto alkyl group, with 0–10 ethylene oxide moieties and 0–1glyceryl moiety.

Stabilizers include one or more members selected from the group consisting of the following members which are selected so that the final amount of stabilizer added is in the range of 0.1–7.0%:

(a) long chain fatty alcohols with greater than 14 carbons, for example C20–40, and mixtures of such long chain fatty alcohols (for example, a C>14 alcohol and ethene homopolymer PETROLITE C-7138 from Petrolite Corporation, St. Louis, Mo.).

(b) acrylates/steareth-20 methacrylate copolymer (for example, ACULYN® 22, from Rohm & Haas, Philadelphia, Pa.); and acrylates copolymer (for example, acrylates copolymer (ACULYN® 33); ACUSOL®-445, -810, and -830; ACRYSOL® ASE 75 from Rohm & Haas); and acrylates/C10–30 alkyl acrylate crosspolymer (PEMULENT™ polymeric emulsifiers from BF Goodrich Company, Brecksville, Ohio, particularly products designated as TR-1 and TR-2). For the acrylates copolymer (ACULYN® 33) product (having a pH in the range of 2.1–3.5), a neutralization step is performed with sodium phosphate (such as disodium phosphate), sodium hydroxide or a cosmetically acceptable organic amine to increase the pH to approximately 6.5.

(c) agents described in U.S. Pat. No. 5,015,415 (incorporated by reference herein) especially N,N-disubstituted phthalamic acids and their ammonium salts selected from the group consisting of Formula III:

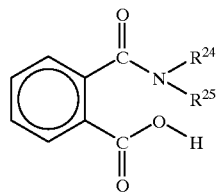

Formula III where $R^{24}$ and $R^{25}$ may be the same or different and are each selected from the group consisting of C10–C40 straight and branched chain alkyl groups, and C10–C40 straight and branched arylalkyl groups (for example, where $R^{24}$ and $R^{25}$ are the same and are each selected from the group consisting of stearyl and hydrogenated tallow such as STEPAN SAB-2 and STEPAN TAB®-2 from Stepan Company, Northfield, Ill.).

The stabilizing agents should be of a grade and purity acceptable for cosmetic use or purified as needed to be cosmetically acceptable. A further discussion of some of these agents may be found in U.S. Pat. No. 5,015,415 to Goze et al and in our copending patent application U.S. Serial Number 08/933,521.

Shampoo carriers which can be used as vehicles for the selected MQ resins described above may be made as solutions, suspensions or emulsions containing a mild, aqueous, foaming and conditioning, detergent composition comprising by weight based on the total weight of the composition:

(a) 4.00–60.00 percent of a detersive surfactant selected from the group consisting of at least one anionic detergent selected from the group consisting of $C_8$–$C_{18}$ alkyl sulfates, $C_8$–$C_{18}$ alkyl ethenoxy ether sulfates containing 1–5 ethenoxy groups in the molecule, $C_{10}$–$C_{18}$ acyl isethionates, $C_{10}$–$C_{20}$ alkyl sulfonates, $C_{10}$–$C_{20}$ alkylene sulfonates, and mixtures thereof; and optionally at least one of:

(i) 0.10–5.00 percent of an anionic hydrotropic, $C_1$–$C_3$ alkyl benzene sulfonate or $C_5$–$C_6$ alkyl sulfate;

(ii) 0.10–15.00 percent of an amphoteric surfactant selected from the group consisting of $C_8$–$C_{18}$ alkyl betaines, $C_8$–$C_{18}$ alkyl sulfobetaines, $C_8$–$C_{18}$ alkylamido $C_2$–$C_3$ alkyl betaines, $C_8$–$C_{18}$ alkylamido $C_2$–$C_3$ alkyl sulfobetaines, $C_8$–$C_{18}$ alkyl amphoacetates, $C_8$–$C_{18}$ alkyl amphopropionates, cocamidopropyl betaine, and mixtures thereof; and (iii) 0.1–4.0 percent of a nonionic surfactant, particularly a member of the group consisting Of $C_8$–$C_{22}$ monoethanolamides and mixtures thereof and $C_8$–$C_{22}$ diethanolamides and mixtures thereof, especially cocamonoethanolamide and cocadiethanolamide; provided that the total amount of detersive surfactant does not exceed 60 percent by weight of the total weight of the composition and, preferably, is in the range of 6–30 percent;

(b) 0.10–7.0 (more particularly 0.10–5.00) percent of a stabilizing agent selected from the group described above as stabilizing agents, particularly polyacrylic acid, derivatives of polyacrylic acid, acrylates copolymer, derivatives of acrylates copolymer, and polymeric emulsifiers such as acrylates/C10–30 alkyl acrylate crosspolymer, with particular products including products with brand names ACULYN® 33, TAB®-

2, SAB-2 and PEMULEN™; mixtures of ACULYN® 22 acrylates/steareth-20 methacrylate copolymer and the ACULYN® 33 product (such as in the range of about 50/50) may also be used;

(c) optionally a quaternized cellulosic polymers (in particular at least one quaternized cellulosic polymer, for example, Polyquaternium-10);

(d) the balance as water or aqueous medium. For conditioning shampoos, optionally another ingredient can be added as (e):

(e) 0.01–10.00 percent of a water-insoluble conditioning agent which is selected from the group consisting of:
  (i) 0.10–6.00 percent of a water-insoluble silicone selected from the group consisting of dimethicones and silicones such as the silicones described in U.S. Pat. No. 4,741,855 incorporated by reference herein; these include polyalkyl siloxanes, polyarylsiloxanes, polyalkylaryl siloxanes, polyestersiloxane copolymers, and mixtures of the foregoing in amounts of from 0.1–10.00%, preferably from about 0.5–5.0%- for example, polydimethyl siloxanes with viscosities at 25 degrees C of 5–600,000 centistokes (for example, 60,000 centistokes) available from the General Electric Company as the Viscasil series and from Dow Corning as the Dow Corning 200 series, polymethylphenylsiloxanes having viscosities of 15–30,000 centistokes at 25 degrees C (for example, SF 1075 methyl phenyl fluid from the General Electric Company and Dow Corning 556 Cosmetic Grade Fluid from Dow Corning), and polypropylene oxide modified dimethylpolysiloxane as well as ethylene oxide or mixtures of EO and PO modified materials;
  (ii) a mixture of at least one of(d)(i) with 0.01–3.00 percent of a cationic polymer such as a polyquaternary compound selected from the group consisting of quaternized cellulosic polymers (in particular at least one quaternized cellulosic polymer, for example, Polyquaternium-10);
  (iii) non-cellulosic quaternium compounds (for example, Polyquaternium-7); and
  (iv) a mixture of at least one of (d)(i) with 0.01–3.00 percent of a cationic polymer such as a polyquaternary compound selected from the group consisting of a mixture of at least one quaternized cellulosic polymer with a non-cellulosic quaternary conditioning polymer. Note that the use of certain silicones may require the use of a suspending or stabilizing agent as described here and in the patent literature.

Another particular type of shampoo can be made by combining from 0.1%–15% of the MQ resin, 4%–60% of a surfactant such as a synthetic surfactant, 0.5–7% of a stabilizer (based on 100% active), and the remainder water. Examples of suitable surfactants include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauroyl sulfate, triethanolamine lauroyl sulfate, triethanolamine lauroyl sulfate, monoethanolamine cocoyl sulfate, monoethanolamine lauroyl sulfate, sodium tridecyl benzene sulfonate and sodium dodecyl benzene sulfonate and others described in U.S. Pat. No. 4,902,499 to Bolich et al at Columns 4–6 incorporated by reference herein.

Another particular example of a suitable vehicle for delivering the formulations of the invention include conditioners. Particular formulations are those made with lipid materials, cationic surfactants and water. Such formulations may be found in U.S. Pat. No. 5,120,531 incorporated by reference herein.

Lipid vehicle materials useful in the invention are water-insoluble compounds possessing both hydrophobic and hydrophilic moieties. Examples of suitable lipid materials are naturally or synthetically derived acids, acid derivatives, alcohols, esters, ethers, ketones, alcohol ethoxylates and amides, with carbon chains of 12–22 and preferably of 12–18 and 16–18 carbons. Specific examples include esters such as cetyl palmitate and glycerylmonostearate; alcohols such as cetyl alcohol and stearyl alcohol. Particular lipid materials are (a) stearyl alcohol as a single lipid material and (b) a mixture of 55–65% cetyl alcohol and the remainder stearyl alcohol. These lipid materials include naturally or synthetically derived fatty alcohols, fatty alcohol ethoxylates, and fatty esters.

Cationic surfactants useful in forming such conditioners include those described in U.S. Pat. No. 5,120,531, referenced above as well as others. Particular examples include cationic surfactants containing amino or quaternary ammonium hydrophilic moieties which are positively charged when dissolved in aqueous compositions such as those of the general formula $(R^{10})(R^{11})(R^{12})(R^{13})N^{+1}$---X, where $R^{10}$ is hydrogen, an aliphatic group of 1–22 carbon atoms, or an aromatic, aryl or alkylaryl group having 12–22 carbon atoms; $R^{11}$ is an aliphatic group having from 1–22 carbon atoms; $R^{12}$ and $R^{13}$ are each independently selected from the group consisting of alkyl groups having 1–3 carbon atoms; and X is an anion selected from the group consisting of halogen, acetate, phosphate, nitrate and alkylsulfate radicals. The aliphatic groups may contain, in addition to carbon and hydrogen atoms, ether linkages and other groups such as amido groups. Examples of quaternary ammonium salts include cetyl trimethyl ammonium chloride ("cetrimonium chloride"), lauryl trimethyl ammonium chloride ("laurtrimonium chloride"), tricetyl methyl ammonium chloride ("tricetylmonium chloride"), stearyidimethyl benzyl ammonium chloride ("stearalkonium chloride"), and di(partially hydrogenated tallow) dimethyl ammonium chloride, distearyldimonium chloride, etc.;

A particular group of conditioning agents are selected from quaternary ammonium compounds, particularly dicetyidimonium chloride, distearyidimonium chloride and other cationic materials as listed above under cationic surfactants.

Examples of conditioners to which the selected MQ resin can be added are those made with 0.1–10.0% lipid material; 0.05–5.0% cationic surfactant and water.

Rinse-off hair care compositions can be formed by combining the MQ resin (or mixtures thereof) as described above with water (preferably distilled or deionized water) or a water/alcohol mixture such as in a ratio of 20:1–1:2 as part of the carrier. From 0.1–10% surfactant is also included. The carrier is present in an amount of from 75%–99.5% by weight, preferably from about 85%–99% and, more particularly, from about 90%–99% of the total composition.

Sprays can be formed by mixing 0.01–10% of the MQ resin (or mixtures thereof) with one or more volatile materials such as water, ethanol, cyclomethicone, as described above with 0.1–10% of at least one surfactant if water is included in a significant amount, and one or more of the optional ingredients described above.

Other particular examples of carriers suitable for applying the volumizing agents of the invention (which may be in the form of shampoos, conditioning agents, conditioning shampoos, sprays and the like) are known to those skilled in the art, for example those described in U.S. Pat. No. 3,577,517 to Kobot et al; U.S. Pat. No. 3,907,984 to Calvert et al; U.S. Pat. No. 4,012,501 to Farber; U.S. Pat. No. 4,223,009 to Chakrabarti et al; and U.S. Pat. No. 4,283,384 to Jacquet et al all of which are incorporated by reference herein.

In addition to the basic formulations described above for shampoos and conditioners, it may also be desirable to add one or more of the following including mixtures of each such ingredients:

(a) viscosity controlling agents for shampoos-polyvinyl alcohol, ethyl alcohol, acrylic acid polymers and copolymers, cellulosic ethers, diethanolamide or monoethanolamide of a long chain fatty acid (for example, PEG 3 lauramide), block polymers of ethylene oxide and propylene oxide, sodium chloride, sodium sulfate, water soluble polymers (such as guar gum) particularly a thickening agent such as hydroxypropylcellulose, guar hydroxypropyltrimonium chloride, PEG-120 methyl glucose dioleate, pentaerythrityl tetrastearate, and xanthan gum.

(a1) viscosity controlling agents for conditioners—polyvinyl alcohol, ethyl alcohol, cellulosic ethers, polyacrylamides, water soluble polymers (such as hydroxyethylcellulose, guar gum, and starch) particularly a thickening agent such as hydroxyethylcellulose, and guar hydroxypropyltrimonium chloride.

(b) fragrances (perfumes) such as cosmetically acceptable fragrances used in hair care products;

(c) preservatives, for example, antimicrobial agents, particularly a mixture of methylchloromethylisothiazolinone and methylisothiazolinone (sold under the tradename KATHON® CG by Rohm and Haas, Philadelphia, Pa.) but also including benzyl alcohol, ethyl paraben, propyl paraben and imidazolidinyl urea, DMDM hydantoin, formalin, 2-bromo-2-nitropropane-1,3-diol ("Bronopol"), and combinations of the foregoing. Particular examples may also include a potentiator such as ethylenediamine tetraacetic acid or the sodium salt form, (for example, Bronopol and EDTA (such as 0.04% Bronopol and 0.1% EDTA); formalin, DMDM hydantoin and EDTA (such as 0.1% formalin, 0.45% DMDM hydantoin, and 0.2% EDTA));

d) dyes or coloring agents, pearlizers (such as ethylene glycol distearate, sodium octyl sulfate, titanium dioxide, or mica), and opacifying agents (such as glycol distearate, fatty ethoxylates, latex opacifiers, stearamide monoethanolamine (MEA) stearate, sodium cetyl stearate and lanolin derivatives) suitable for use in hair care products;

(e) pH adjusting agents such as citric acid, sodium carbonate, etc.;

(f) sequestering agents such as ethylene diamine tetraacetic acid and sodium salts of the foregoing. Such additives may be included on an individual basis in appropriate amounts, for example in the range of about 0.01%–60%, preferably from abut 0.5%–40% by weight of the total weight of the composition.

It will be appreciated by those skilled in the art that compositions formulated according to this invention may result in an enduring volumizing effect over time so that the use of products made according to the invention may be alternated with other types of commercial shampoos to achieve and maintain the desired level of volumizing. While the increase in hair volume will vary from person to person, generally volume increases in the range of 10–40% as measured by the Mannequin volume test described below may be obtained by consistent use of the compositions of this invention. In general, the effect on thin, fine hair will be more pronounced than on thick, long, coarse hair.

It should also be noted that the compositions of this invention provide volumizing effects without substantial fixative character (stickiness) or chemical adhesion between the hair fibers. Thus the hair may be restyled by recombing or refluffing. Such a procedure would not be effective with fixative-treated hair since it would result in breaking of the spot welds formed between hairs by the fixative and the consequent loss of the fixative styling effect. The lack of fixative character in compositions of the present invention may be evaluated by curl retention tests, one of which is described below.

Examples of formulations which may be made in accordance with the present invention include the following:
Shampoos:
Formulation A
0.1–7.5%, particularly 0.1–5%, and more particularly 0.25–2.5% of a selected liquid MQ resin(s), and the remainder as a shampoo vehicle. For conditioning shampoos from 0.1–3.0%, particularly 0.1–2.0% of a conditioning agent may also be included.

Formulation B
10–18% of a surfactant, especially an anionic surfactant selected from the group consisting of ammonium lauryl sulfate, ammonium laureth sulfate, sodium lauryl ether sulfate, sodium laureth ether sulfate, ammonium lauryl ether sulfate, ammonium laureth ether sulfate and mixtures of the foregoing;
0.25–2.5% of a selected MQ resin;
0.10–5.00% of a stabilizing agent;
1–3% of an ingredient that functions as a foam modifier and/or a viscosity modifier (for example, at least one member selected from the group consisting of cocamidodiethanolamine, cocamidomonoethanolamine and cocamidopropyl betaine); and the remainder water or other aqueous medium which medium may include an effective amount of a preservative as well as fragrance and coloring agents.

Formulation C
10–20% of a mixed surfactant system comprising at least one anionic and at least one amphoteric surfactant in a ratio of 60:40–40:60 (examples of suitable anionics are the same as described in Formula B and examples of suitable amphoterics are cocamidopropyl betaine and cocamidopropyl amine oxide); 0.25–2.5% of a selected MQ resin;
0.10–5.00% of a stabilizing agent; and the remainder water or other aqueous medium which medium may include an effective amount of a preservative as well as fragrance and coloring agents.

Conditioners:
0.1–7.5%, particularly 0.1–5% and more particularly 0.2–2.5% of a selected liquid MQ resin(s), and the remainder as a carrier for the composition.

Formulation D
1–4% of a lipid material (for example, stearyl alcohol, and mixtures of stearyl and cetyl alcohols);
1–3% of a quaternized compound (for example at least one of dicetyidimonium chloride; distearyldimonium chloride;

and cetyltrimonium chloride); and the remainder water or other aqueous medium which medium may include an effective amount of a preservative as well as fragrance and coloring agents.

Volumizing Sprays:
0.01–7.5%, particularly 0.03–5.0% and, more particularly, 0.05–2.0% of a selected MQ resin with a volatile carrier such as ethanol.

Volumizing Rinses:
0.1–7.5%, particularly 0.1–5.0% and, more particularly, 0.2–2.5% of a selected MQ resin with a carrier such as water with a suitable amount of surfactant/stabilizer (for example ceteth-20 and cetrimonium chloride), to keep the emulsion stable (amount of stabilizer being dependent upon the amount of MQ resin used).

Hair Sprays with Fixative Additive:
0.01–7.5%, particularly 0.05–2.0% of a selected liquid MQ resin(s);
0.1–20%, particularly 0.5–15% of a volatile carrier;
72.5–99.89%, particularly 83–99.45% of a fixative vehicle (which itself may contain a volatile carrier such as ethanol); where each of the ingredients may be a single ingredient or mixtures thereof.

In general the compositions of the present invention may be made by conventional adding and mixing techniques. The MQ resin may be added in several ways. In the case of shampoo formulations, the MQ resin can be added separately, either alone or mixed with cyclomethicone or dimethicone as in the following examples. Alternatively, the MQ resin can be added to the heated oil phase prior to any emulsion formation.

The compositions of the present invention makes it easier for the hair to retain a particular style or configuration. Remarkably, the use of such compositions does not interfere with grooming and appears to be unaffected by the presence of conditioning agents. Also, tests have shown that volume increases did not diminish with repeated use as can happen with fixatives that build up on the hair.

Another feature of the invention is the ability to be formulated in compositions that are rinsed off of the hair. Thus, while fixative-based volumizers are usually formulated as leave-in products, such is not the case with the present invention which may be formulated either as leave-in or rinse-off products.

The compositions of this invention can also be used in combination with fixatives without loss of volumizing effect. Tests have shown that the MQ resins described here do not appear to interfere with the action of the fixatives.

While the compositions of this invention have been described in terms of "comprising" it is also intended that the compositions include narrower compositions in terms of "consisting of" and consisting essentially of". Also, while the compositions of the invention have been described as "comprising" it is to be understood that the compositions also include those made by combining the ingredients listed in the composition.

EXAMPLES

The following Examples are included as being illustrative of the invention but should not be construed as limitations thereon. Unless otherwise indicated, all percents are in weight percents based on 100% active level for all ingredients and all chemical and scientific terms have their usual and customary meanings. All temperatures are in degrees C. These conventions are also used throughout the rest of the patent application.

Examples 1–4 Conditioning Formulations

Conditioning formulations were made using the types and amounts of materials listed in Table I. In a suitable vessel, the hydroxyethylcellulose was dispersed in the distilled water at room temperature. The C9–11alcohol ethoxylate (EO 6:1) ("C9–11Pareth-6") was then added with mixing, and the resulting solution was heated to 75 degrees C. The ceteth-20, steareth-20, stearyl alcohol, isostearamidopropyl dimethylamine, and dicetyldimonium chloride were combined in a suitable vessel and heated to 75 degrees C with mixing. With both solutions at 75 degrees C, the water phase was then added to the oil phase with mixing. The resulting emulsion was stirred at 75 degrees C for 10 minutes and then cooled to 60 degrees C. The liquid trimethylsiloxysilicate was dissolved in the cyclomethicone and added to the emulsion at 62 degrees C. The emulsion was then cooled to 38 degrees C at which temperature the fragrance and preservative were added. The final formulation was lastly cooled to room temperature. The MQ resin used was a trimethylsiloxysilicate ("MQ-A") obtained from GE.

TABLE I

| Material | Example 1 Weight % | Example 2 Weight % | Example 3 Weight % | Example 4 Weight % |
|---|---|---|---|---|
| Distilled water | 93.85% | 93.85% | 93.85% | 93.85% |
| Hydroxyethylcellulose | 0.50 | 1.00 | 1.0 | 1.0 |
| C9-11 Pareth-6 | 0.20 | 0.20 | 0.20 | 0.20 |
| Ceteth-20 | 0.50 | 0.50 | 0.50 | 0.50 |
| Steareth-20 | 0.50 | 0.50 | 0.50 | 0.50 |
| Stearyl Alcohol | 2.00 | 2.00 | 2.00 | 2.00 |
| Isostearamidopropyl dimethylamine | 0.80 | 0.80 | 0.80 | 0.80 |
| Dicetyldimonium chloride | 1.50 | 1.50 | 1.50 | 1.50 |
| Liquid trimethyl-siloxysilicate | 2.50 | 2.50 | 0.75 | 1.5 |
| Cyclomethicone (D5) | 2.50 | 2.50 | 2.50 | 2.50 |
| Fragrance | 0.75 | 0.75 | 0.75 | 0.75 |
| Methylchloromethyl-isothiazolinone and methylisothiazolinone | 0.07 | 0.07 | 0.07 | 0.07 |

Example 5 Conditioning Formulation

A 300 g sample of a conditioning formulation was made with the following materials: 0.50% hydroxyethylcellulose; 93.35% distilled water, 2.75% Cetearyl alcohol; 0.50% stearamidopropyl dimethylamine; 0.15% polyglyceryl-3 diisostearate; 0.25% citric acid; 0.20 methyldibromoglutaronitrile and phenoxyethanol (MERGUARDOR® 1200 from Calgon Corporation, Pittsburgh, Pa.); 0.15% glyceryl monostearate; 1.50% distearyldimonium chloride;0.25% of the MQ resin described in Examples 1–4; 0.40% fragrance. In a suitable vessel the hydroxyethylcellulose and distilled water were combined with mixing. The solution was heated to 80 degrees C. The cetearyl alcohol, distearyldimonium chloride, stearamidopropyl dimethylamine, glyceryl monostearate and polyglyceryl-3 diisostearate were combined in a separate vessel and heated to 80 degrees C with mixing. When both mixtures reached 80 degrees C, the aqueous phase was added to the oil phase with stirring. The resulting emulsion was cooled to 60 degrees C, and the silicone MQ resin was added with stirring. When the temperature reached 38 degrees C the fragrance and preservative were added. The final formulation was then cooled to room temperature.

Examples 6–7 Shampoo Formulations

Shampoo formulations were made using the types and amounts of materials described in Table II. In a suitable vessel was combined all but 10 weight percent of the distilled water, the tetrasodium EDTA, sodium phosphate dibasic ("disodium phosphate"), ammonium lauryl sulfate, sodium deceth-3 sulfate, sodium cumene-sulfonate, and cocamidopropyl betaine. The resulting solution was heated to 90 degrees C with stirring. In a small container was combined the remaining 10 weight percent of the distilled water and the Polyquaternium-10. The contents of the small container were then added to the above solution as it was heating. The isosteareth-2, C20–40 alcohols, and distearyldimonium chloride were combined and melted in a suitable vessel. Once melted, this mixture was added to the aqueous solution at 90 degrees C with stirring. The resulting emulsion was then cooled to 60 degrees C. The liquid trimethylsiloxysilicate (same MQ resin as described in Examples 1–4) was dissolved in cyclomethicone and added to the emulsion at 60 degrees C with mixing. The resulting mixture was then cooled to 38 degrees C at which temperature the fragrance and preservative were added. The final formulation was then cooled to room temperature. Note that for Example 7 this procedure was used but there was no sodium deceth-3 sulfate, isosteareth-2, distearyldimonium chloride or cyclomethicone used.

TABLE II

| Materials | Example 6 Weight % | Example 7 Weight % |
|---|---|---|
| Distilled Water | q.s. | q.s. |
| Tetrasodium EDTA | 0.10 | 0.10 |
| Disodium phosphate | 0.20 | 0.20 |
| Ammonium lauryl sulfate | 3.36 | 8.26 |
| Sodium deceth-3 sulfate | 4.50 | 0 |
| Sodium cumenesulfonate | 2.80 | 0.66 |
| Cocamidopropyl betaine | 9.00 | 9.00 |
| Polyquaternium-10 | 0.90 | 0.55 |
| Isosteareth-2 | 0.80 | 0.00 |
| C20-40 alcohols | 4.00 | 2.00 |
| Distearyldimonium chloride | 1.00 | 0.00 |
| Liquid trimethylsiloxysilicate | 2.50 | 1.00 |
| Cyclomethicone (D5) | 2.50 | 0.00 |
| Fragrance | 1.20 | 0.75 |
| Methylchloromethylisothiazolinone and methylisothiazolinone | 0.07 | 0.07 |

Examples 8–9 Shampoo Formulations

Shampoo formulations were made using the types and amounts of materials listed in Table III. In a suitable vessel all but 10% of the distilled water and the sodium phosphate were combined and mixed for 10 minutes. The ammonium lauryl sulfate was added to the vessel and mixed for 5 minutes. The resulting solution was heated to 50 degrees C. The remaining portion of distilled water and the Polyquaternium-10 were premixed for 1–2 minutes and added to the vessel with mixing for an additional 15 minutes. In a separate vessel the cocadiethanolamide ("cocamide DEA"), guar gum and distearyldimonium chloride were combined and heated to 50 degrees C with occasional stirring. When both vessels reached 50 degrees C, they were combined with mixing. The silicone MQ resin (the same resin as described in Examples 1–4) and dimethicone (if included in the formulation) were added separately to the vessel and mixed for 15 minutes. The vessel was then allowed to begin cooling. The acrylates copolymer ("ACULYN® 33") and fragrance were premixed, and added to the emulsion. When the temperature of the mixture reached 38 degrees C, the preservative was added. The final formulation was then cooled to room temperature.

TABLE III

| Materials | Example 8 Weight % | Example 9 Weight % |
|---|---|---|
| Distilled water | q.s. | q.s. |
| Ammonium lauryl sulfate | 16.80 | 16.80 |
| Sodium phosphate monobasic | 0.30 | 0.30 |
| Polyquaternium-10 | 0.25 | 0.25 |
| Cocodiethanolamide | 2.00 | 2.00 |
| Guar gum | 0.22 | 0.22 |
| Distearyldimonium chloride | 0.25 | 0.25 |
| Dimethicone | 0.00 | 1.00 |
| MQ Resin | 2.50 | 2.50 |
| Acrylates copolymer | 1.65 | 1.65 |
| Fragrance | 0.75 | 0.75 |
| Methylchloromethylisothiazolinone and methylisothiazolinone | 0.07 | 0.07 |

Examples 10–11 Shampoo Formulations

In a suitable vessel, all but 10% of the distilled water and the sodium phosphate were combined. The ammonium lauryl sulfate was added with mixing. The resulting solution was heated to 90 degrees C. The remaining portion of distilled water and the Polyquaternium 10 were premixed in a separate container for 1–2 minutes and added to the solution with mixing for an additional 15 minutes. In separate vessel, the cocadiethanolamide, C20–40 alcohols and distearyldimonium chloride were melted and added to the solution with mixing. The resulting emulsion was then allowed to cool. The silicone MQ resin (same resin as described in Examples 1–4) and dimethicone (if used in the formulation) were added separately to the solution at 60 degrees C with mixing. When the temperature of the emulsion reached 38 degrees C, the fragrance and preservative were added. The final formulation was then cooled to room temperature.

TABLE IV

| Materials | Example 10 Weight % | Example 11 Weight % |
|---|---|---|
| Distilled water | q.s. | q.s. |
| Ammonium lauryl sulfate | 16.80 | 16.80 |
| Sodium phosphate | 0.30 | 0.30 |
| Polyquaternium-10 | 0.25 | 0.25 |
| Cocadiethanolamide | 2.00 | 2.00 |
| C20-40 alcohols | 2.00 | 2.00 |
| Distearyldimonium chloride | 0.25 | 0.25 |
| Dimethicone | 0.00 | 1.00 |
| MQ Resin | 2.50 | 2.50 |
| Fragrance | 0.75 | 0.75 |
| Methylchloromethylisothiazolinone and methylisothiazolinone | 0.07 | 0.07 |

Examples 12–13 Shampoo Formulations

In a suitable vessel all but 10 weight percent of the distilled water, and the sodium phosphate monobasic were combined with mixing. The ammonium lauryl sulfate was added with mixing. The resulting solution was heated to 60 degrees C. In a small container the remaining 10 weight percent of the distilled water and the Polyquaternium-10 were combined. The contents of the small container were then added to the above solution as it was heating with mixing for an additional 15 minutes. In a separate vessel the cocadiethanolamide, guar gum and the distearyldimonium chloride were combined and melted. Once melted, this mixture was added to the aqueous solution at 60 degrees C with stirring. The silicone MQ resin (same resin as described in Examples 1–4) and dimethicone (if included in the formulation) were added separately to the emulsion with mixing. Distearyl phthalic acid amide (TAB-2) was melted in a separate container and added to the mixture when cooled to 55 degrees C. The resulting mixture was then cooled to 38 degrees C at which temperature the fragrance and preservative were added. The final formulation was then cooled to room temperature.

TABLE V

| Materials | Example 12 Weight % | Example 13 Weight % |
| --- | --- | --- |
| Distilled water | q.s. | q.s. |
| Ammonium lauryl sulfate | 16.80 | 16.80 |
| Sodium phosphate | 0.30 | 0.30 |
| Polyquaternium-10 | 0.25 | 0.25 |
| Cocadiethanolamide | 2.00 | 2.00 |
| Guar gum | 0.22 | 0.22 |
| Distearyldimonium chloride | 0.25 | 0.25 |
| Dimethicone | 0.00 | 1.00 |
| MQ Resin | 1.00 | 1.00 |
| fragrance | 0.75 | 0.75 |
| Methylchloromethylisothiazolinone and methylisothiazolinone | 0.07 | 0.07 |
| Distearyl phthalic acid amide | 2.00 | 2.00 |

Examples 14–15 Shampoo Formulations

In a suitable vessel all but 10 weight percent of the distilled water, and the acrylates C10–30 alkyl acrylate crosspolymer (PEMULEN™ TR-1) were combined with mixing. The ammonium lauryl sulfate was then added with additional mixing, followed by the sodium phosphate. In a small container the remaining 10 weight percent of the distilled water and the Polyquaternium-10 were combined. The contents of the small container were then added to the above solution with mixing for an additional 15 minutes. In a separate vessel the cocadiethanolamide, guar gum, fragrance and the distearyldimonium chloride were combined and added slowly to the solution and allowed to mix thoroughly. The silicone MQ resin (same resin as described in Examples 1–4) and dimethicone (if included in the formulation) were added separately to the emulsion with continued mixing. The preservative was then added to obtain the final formulation. (Note that throughout this example heating was used in about the same way as described in Examples 12–13.) The final formulation was cooled to room temperature.

TABLE VI

| Materials | Example 14 Weight % | Example 15 Weight % |
| --- | --- | --- |
| Distilled water | q.s. | q.s. |
| Ammonium lauryl sulfate | 55.00 | 55.00 |
| Sodium phosphate | 0.30 | 0.30 |
| Polyquaternium-10 | 0.20 | 0.20 |
| Cododiethanolamide | 2.00 | 2.00 |
| Guar gum | 0.15 | 0.15 |
| Distearyldimonium chloride | 0.25 | 0.25 |
| Dimethicone | 0.00 | 0.75 |
| Silicon MQ Resin | 2.25 | 2.25 |
| fragrance | 0.75 | 0.75 |
| Methylchloromethylisothiazolinone and methylisothiazolinone | 0.07 | 0.07 |
| Acrylates C10-30 alkyl acrylate crosspolymer | 0.30 | 0.30 |

Example 16 Spray Formulation

A spray formulation may be made with the following ingredients: 0.17% dimethicone copolyol; 0.2% cyclomethicone (pentamer); 0.001octyl salicylate; 0.001% benzophenone-3; 0.001hydrolyzed animal keratin; 0.35% fragrance; 1.0% MQ resin (the same type as used in Examples 1–4) and q.s. ethanol (for example 95%). The SD alcohol and the trimethylsiloxysilicate were combined in an a suitable vessel. The dimethicone copolyol, cyclomethicone, octyl salicylate, benzophenone-3, hydrolyzed keratin and the fragrance were added to the solution and the resulting mixture was placed in spray pump bottles.

PERFORMANCE EVALUATIONS

Performance evaluations were done for volume increase and adhesive properties as well as aesthetics. The following Examples describe these evaluations.

Control Conditioner for Mannequin Test: Example A

A control sample was made using the following ingredients: Part 1–4.50% cetyl alcohol; 2.50% stearyl alcohol; 2.40 glyceryl monostearate; 1.00% cyclomethicone; 0.50% of a mixture of polysorbate 80, cetyl acetate, and acetylated lanolin alcohol (SOLULAN 98, from Amerchol Corporation, Danbury, Conn.); 1.50% mineral oil; 2.50% white petrolatum; 0.50% propylene glycol; Part 2-q.s. deionized water, 4.00% dodecyltrimonium chloride in aqueous isopropanol (ARQUAD® 12–50 from Akzo, Chicago, Ill.); Part 3–0.50% diazolidinyl urea; 0.75% fragrance. All the materials in Part 1 were combined with stirring and heated to 80 degrees. All the materials in Part 2 were combined in a separate vessel with stirring and heated to 8–0 degrees C. With both parts at 80 degrees C, the Part 1mixture was added to the Part 2 mixture with stirring at 80 degrees C for 10 minutes and then cooled to 40 degrees C. When the combined mixture was at 40 degrees C, the ingredients from Part 3 were added and mixed until the entire mixture was homogeneous. The resulting mixture was then cooled to room temperature.

Mannequin Volume Test

It was ascertained that a reliable test was needed to evaluate volume using a test that correlated more closely with real life results on human heads. The Mannequin Volume Test was developed to meet this requirement.

Volume on heads of hair is associated with the volume of the total assembly of hair fibers on the head, not the volume of individual fibers. Depending upon the particular style and the length of the hair, an individual fiber on a head of hair is in contact with and helps support several other fibers, thus contributing to maintaining the architecture of the hair as a whole. For example, fine hair is less able to support its own weight or the weight of other hairs. As a result, the entire hair assembly lies flatter on the head and, thus, occupies less volume. In view of the association of hair volume with the architecture of the hair as a whole, any test for hair volume, in order to be predictive of volume on real heads of hair, must employ as a model, assemblies of hair fibers in a configuration similar to that of hair on an actual head. Most current methods do not use this criteria since many of them rely on volume measurements of single fibers, assemblies of unsecured fibers, or tresses of hair. Since all the fibers in a tress are secured together at one end, rather than being individually secured at many thousands of points over an entire head of hair, the hair fibers in a tress cannot assume a space filling architecture, as on a head of hair, in which individual hairs support each other, thus creating volume. Volume measurements on tresses, therefore, would not be expected to be very predictive of volume changes on real heads of hair.

In British Patent 2,297,757 is described a modified procedure of Robbins and Crawford in which measurements on hair tresses provide the data for analysis. Again, since there is not really an opportunity for hair fibers in the tress to form the space filling assemblies of fibers, or styles, found on a head of hair, one would not expect results with this method to necessarily correlate with consumers' experiences on real heads of hair.

For the laboratory work done on the compositions of this invention, volume measurements were made on mannequin heads having real human hair secured at many points over the entire mannequin head. This hair can therefore assume the same types of volume filling configurations formed on human heads. Half-head tests on human subjects in the salon and extended home use tests involving human females, confirm that the Mannequin Volume Test is very predictive of actual volume changes on consumers' heads.

The Mannequin Volume Test utilizes traditional salon half head test methodologies as well as image analysis techniques to quantify volume changes. In this test, before treatment volume measurements were taken for the hair sections on each side of the head to eliminate any bias that might occur from unequal amounts of hair between the two hair sections. The heads were then treated and dried. All formulae in this invention were tested against a light conditioner formula. It was necessary to use a conditioning formula as a control to eliminate any volume increases that would occur from the frictional damage that occurs during grooming of the mannequin head. Tangles or the roughening of the hair surface is a widely accepted method of increasing hair volume. The technique of teasing the hair has been used for decades to generate large increases in hair volume. That the control conditioner did not negatively affect hair volume is documented in the following results. All volume changes measured for the control treatment were positive, indicating that the volume after treatment was never less than before treatment. (Note that the volumes before treatment were that of clean hair.)

In order to demonstrate that the conditioner control (Example A) did not decrease volume, a series of experiments were run to validate the use of a light conditioner formulation as the control. For the conditioning formulations a composition made according to Example 1 without the MQ resin was tested against the light conditioning formulation made in Example A. There was no significant difference in the results (-4.8% difference with a p-value of 0.27). For the shampoo studies the same logic was used; a composition made according to Example A was tested against a formulation made according to Example 8 but without the MQ resin. There was no significant difference in the measured volumes provided by the two formulations (3% difference, p value equals 0.73), confirming that the conditioner control did not cause a decrease in hair volume.

Mannequin heads used in volume experiments were "Sarah" heads purchased from Pivot Point International, Chicago, Ill. Prior to experimental treatment, mannequin heads were cleaned with a detergent solution consisting of 20% SLES-2EO, 5% cocamidopropylbetaine, and 0.8% sodium cumene sulfonate. To minimize tangling, the detergent was worked into the hair with a vent brush. The heads were then rinsed under running water set to 38 degrees C (100 degrees F) until the rinse water was clear. Mannequin heads were washed twice, once with 5 ml of detergent solution and then again with 2.5 ml of solution. Following washing, the mannequin hair was detangled with a brush and then combed straight. The hair was then allowed to dry overnight. The hair on the washed mannequins must be combed as flat as possible so that the intrinsic volume measured at this stage contains minimal contributions from hair style. In volume experiments, the two sides of the mannequin heads were treated separately. Each side was first wet with 38 degree C (100 degree F) water and then treated with 3 ml of either a control or a volume formulation. The side to which the volume formulation was applied was alternated with each new head tested. Following application, test formulations were rubbed into the hair for 30 seconds and then rinsed under 38 degrees C (100 degree F) water until rinse water was clear and a minimum of 60 seconds has elapsed. For experiments in which the volume formulation was applied and rinsed more than once, all applications were run on one side consecutively rather than alternating applications on the two sides of the head. For conditioners containing the MQ resin (Examples 1–5), one application was used followed by volume measurements. For shampoos containing the MQ resin (Examples 7–15), 3 washes with the shampoo were performed prior to taking the volume measurements. For Example 6 only one wash was performed. Apparent changes on mannequin heads were measured using a Zeiss Kontron image analyzer connected to a Sony XC-77CE miniature CCD video camera module with a 60 mm Nikon AF Micro-Nikkor lens. The mannequin image was captured by the video camera, digitized, and areas of each side measured using a program written for this purpose. Apparent changes in volume were estimated by measuring mannequin heads after cleaning, treating the heads, and remeasuring. The percent change in volume for each side was calculated using the formula:

Change in $V_{side}=100\times[V_{side}(after)-V_{side}(before)]/V_{side}(before)$ where $V_{side}$ is the apparent volume measured for a particular side of the head, while before and after refer to the values measured before and after treatment. The percent volume change for a particular treatment is then represented by the formula $\Delta V=\Delta V_{treatment}-\Delta V_{control}$. In determining volume changes for a particular treatment, measurements were performed on a minimum of 5 heads per experiment. Data for control and treatment sides were then evaluated using a paired t test. Results may also include "p" values as is accepted statistical practice; a p value greater than 0.05 indicates that the data is not statistically significant at a 95% confidence level.

Volume data was obtained for the formulations described in Examples 1–15. The data is listed in Table VII. Note that the date reflects an average of at least 5 evaluations.

TABLE VII

| Example | % Volume Increase | p-value |
|---|---|---|
| 1 | 24.4 | 0.039 |
| 2 | 21.9 | 0.032 |
| 3 | — | — |
| 4 | 20.7 | 0.008 |
| 5 | 26.1 | 0.014 |
| 6 | 37.3 | 0.058 |
| 7 | 21.8 | 0.025 |
| 8 | 20.0 | 0.044 |
| 9 | 20.7 | 0.003 |
| 10 | 16.7 | 0.045 |
| 11 | — | — |
| 12 | 20.1 | 0.017 |
| 13 | — | — |
| 14 | 29.2 | 0.007 |
| 15 | 21.1 | 0.020 |

The volume increases reported in Table VII are almost all statistically significant (p<0.05). The magnitudes of the volume increases, 16.6%–37.3%, indicate that the compositions of the current invention are very effective in producing noticeable increases in hair volume.

Evidence tha the observed volume increases came from the MQ resin, MQ-A and not from the carrier is provided by the results of an experiment in which the conditioning formula without Example 1was compared in a mannequin volume test to the same formula without the MQ resin. Compared to the conditioner minus MQ treated side, a 25% increase in volume was observed for the side treated with the MQ-contaiging formula, confirming that volume came from the resin, not from the carrier.

Human Testing

Further support for the volumizing efficacy of the formulas of this invention can be provided by testing on human subjects. In separate tests, human female subjects were given test samples of either the volumizing conditioner of Example 1, or the volumizing shampoo of Example 9. Subjects were instructed to use the test product for a period of 5 days in the case of the conditioner and 10 days in the case of the shampoo.

The subjects recorded their evaluation of the effect of the test products on hair volume in comparison to their regular hair volume. For the evaluation, they used a scale of 1to 5, 1 equaling significantly less volume and 5 equaling significantly more volume. The data were collected and then analyzed using the Wilcoxon Signed Rank Test as described in *Practical Nonparametric Statistics,2$^{nd}$* ed., W. J. Conover, John Wiley and Sons, 1980. The results showed that a significant increase in hair volume was provided by both the conditioner and shampoo test products at a 95% confidence level.

Curl Retention

Three tresses of clean European hair (3.5 g each) were prepared for each experimental treatment. Prior to treatments the uncurled length ($L_u$) was measured for each tress. Tresses were then wet with water, combed free of snarls, and then squeezed free of excess water between the thumb and index finger of a gloved hand. Following this, tresses were hung from the root end and curled with a standard 2.22 cm (⅞ inch) plastic curler, secured with the plastic clip provided with the curler, and allowed to dry for a minimum of sixteen hours. After drying, the plastic curlers were carefully removed from the tresses, which were then treated with a 2.5% solution of test MQ resin dissolved in toluene. This solvent was used because it formed a solution with the MQ resins tested. Test solutions were sprayed onto the tresses using a Seaquist P22/290 pump that delivered about 0.25 g of solution per actuation. To ensure uniform application, tresses were sprayed from a distance of 15 cm (6 inches). Each tress was sprayed four times in the front and four times in the back, resulting in a total application of two grams of solution. Freshly sprayed tresses were laid on a wire rack and permitted to dry for one hour. Following this, they were hung in a humidity chamber at 21 degrees C and 80% relative humidity . Length measurements were recorded at 0, 0.25, 0.5, 1, 2, 3, 4 and 24 hours. Percent curl retention for each reading was calculated using the following formula:

Percent Curl Retention=[$L_u$-L(t)]/[$L_u$-L(0)], where $L_u$ is the length of the uncurled hair, L(t) is the length of the hair at time t, and L(0) is the length of the hair at time zero. Data is shown in Table VIII. Entries are "percent curl retention". All MQ resins used were obtained from the General Electric Company.

TABLE VIII

| MQ Resin | 15 minutes | 1 hour | 4 hours | 24 hours |
| --- | --- | --- | --- | --- |
| 50% solution of solid trimethylsiloxysilicate in cyclomethicone (MQ-B)[a,d] | 43.3* | 39.8* | 35.0* | 34.1* |
| trimethylsiloxysilicate (MQ-A)[a] | 2.2 | −6.1 | −5.5 | −5.1 |
| tetradecyldimethyl- siloxysilicate (MQ-D)[a,b] | 2.4 | 2.5 | 3.6 | 4.1 |
| octadecyldimethyl- siloxysilicate (MQ-E)[a,b] | 24.3* | 3.0 | 3.4 | 4.5 |
| (C16-18) alkyldimethyl- siloxysilicate (MQ-G)[a,b,e] | 11.6 | 8.3 | 4.3 | 4.2 |
| C20-24 dimethyl- siloxysilicate (MQ-F)[a,b] | 9.7 | 2.1 | 2.0 | 3.1 |
| poly(oxyethylene)dimethyl- siloxysilicate (MQ-H)[a,c,e] | 15.9* | 16.3* | 9.7 | 7.8 |

[a]Obtained from General Electric Company.
[b]Each M unit of polymer is substituted with a long chain alkyl group.
[c]Each M unit of polymer is substituted with a poly(oxyethylene) group of from 12–13 oxyethylene units per group.
[d]Commercial product from General Electric.
[e]Described in U.S. Pat. No. 5,684,112.

All curl retentions have had toluene control values subtracted. Statistically significant entries are marked with an asterisk.

Of the MQ resins listed in Table VIII, only the "MQ-B" exhibited significant curl retention over the entire 24 hours of the experiment. This indicates that this resin has significant adhesive character. A fixative mechanism could, therefore, be contributing to the volume increases listed for this resin in Table IX.

The liquid MQ "MQ-A", on the other hand, exhibited no significant curl retention and, therefore, no significant adhesive character. Despite this lack of adhesion, the liquid MQ, remarkably, still provides significant volume as seen by the examples in Table VII.

SUMMARY EXAMPLES

By way of Summary Examples, Table IX lists volume measurements done on the MQ resins described in Table VIII where each of the MQ resins have been formulated in one or both of the shampoo formulation of Example 8 and the conditioner formulation of Example 1. For these formulations the level of addition of the MQ resin was 2.5% active material.

The data in the column labeled "Amount of Deposit" in Table IX is actually a relative deposition value and was obtained on wool swatches (7 cm ×11 cm) which were wet in 38 degrees C running tap water, treated for 1 minute with 1 ml amounts of a test product (either shampoo containing test MQ resin or conditioner containing test MQ resin), and then rinsed for 1 minute under 38 degree C running tap water. MQ resin deposition was then measured using ESCA (Electron Spectroscopy for Chemical Analysis), a technique known to those skilled in the art. ESCA is used to qualitatively and quantitatively determine the elemental composition of solid surfaces. The solid surface on which the products were tested was wool. Wool is often used as a substitute for human hair because it is similar both chemically and morphologically to human hair and also because of the greater ease in measurements on wool as compared to human hair. As is known to those skilled in the art, ESCA uses the photoelectric effect to obtain information about the chemical composition of the solid surface. The sample surface is irradiated by x-ray photons which interact with atoms in the surface of the material. If the photons are of sufficient energy, electrons are emitted from the orbitals of the surface atoms. The kinetic energies of these emitted photoelectrons are then measured by an electron spectrometer. The relationship that describes this process is: BE=x-ray energy −KE, where KE and BE are the measured kinetic energy and the calculated binding energy of the emitted photoelectron, respectively. The electron binding energy is characteristic of the element and electronic subshell from which it is emitted and serve to identify different elements on solid surfaces. The characteristic peak of the MQ resin was first determined using the pure substance. The areas of the peaks present on the test sample were used to determine the relative concentrations of the elements in the sample surface. For MQ resin deposition, the Si peak shows up in a distinct shape which helps distinguish MQ resins from other silicones such as dimethicone. The area under the peak allows for the calculation of the percent Si present. For each sample tested, 3 replicate wool swatches are prepared. Of the three swatches, 2 are analyzed initially. If there is a large variance in the 2 measurements, a third sample is run for verification. This process was run on the Examples listed in Table IX. The values in the column for Amount of deposition column were calculated by dividing the measured deposition of a particular MQ resin on the wool swatches by the deposition on wool of the trimethylsiloxysilicate resin (MQ-A). These values are, thus, the relative depositions of the various resins compared to the MQ-A resins.

nolamide; 0.22% guar gum; 0.25% distearyidimonium chloride; 0.50% disteryl phthalic acid amide; 1.76% sodium cumene sulfonate; 0.75% fragrance; 0.07% preservative (KATHON CG) in addition to the amounts of ingredients shown in Table X. The distilled water was used in an amount to make 100% (q.s.). Note that MQ-A is the same MQ-A described in earlier examples.

TABLE X

| Ingredient | Ex. 16 | Ex. 17 |
|---|---|---|
| MQ resin (MQ-A) | 0.75 | 0.60 |
| Dimethicone | 1.00 | 2.00 |
| ACULYN 22 | 0.90 | 0.90 |
| ACULYN 33 | 0.84 | 0.84 |
| distilled water | q.s. | q.s. |

In a suitable vessel all but 10% of the distilled water and the sodium phosphate were combined, mixed for 10 minutes and heated to 50 degrees C. The ACULYN® 22 acrylates material, ACULYN® 33 acrylates copolymer, and the ammonium lauryl sulfate were added to the vessel, the pH was increased to 7.0 using 50% sodium hydroxide, and the ingredients were mixed for 10 minutes. The sodium cumene sulfonate was added and mixed until uniform. The pH was then decreased to 6.0–6.5 using 50% citric acid. The remaining portion of the distilled water and the Polyquaternium-10 were premixed for 1–2 minutes and added to the vessel. In

TABLE IX

| Description | Form | M:Q Ratio | Viscosity | Results (Volume change) | | p-values (Volume change) | Amount of deposit |
|---|---|---|---|---|---|---|---|
| trimethylsiloxysilicate (MQ-A) | liquid | 1:1 | 4500–12,000 cP | shampoo | +20% | 0.044 | 1 |
| | | | | conditioner | +24.4% | 0.039 | 1 |
| 50% solution of solid trimethylsiloxysilicate in cyclomethicone (MQ-B) | solid dissolved in cyclo-methicone | 0.7:1 | solid | shampoo | +31.1% | 0.002 | 0.80 |
| | | | | conditioner | +21.4% | 0.066 | 0.70 |
| Tetradecyldimethylsiloxy-silicate (MQ-D) | liquid | 2:1 | 50 cP | shampoo | −2.8% | 0.52 | 1.57 |
| Octadecyldimethylsiloxy-silicate (MQ-E) | solid (waxy) | 2:1 | solid | shampoo | +2.1% | 0.67 | 1.71 |
| | | | | conditioner | +8% | 0.37 | 0.68 |
| (C20–C24) alkyldimethyl-siloxysilicate (MQ-F) | solid (waxy) | 2:1 2:1 | solid | shampoo | +6.4% | 0.30 | 2.40 |
| | | | | conditioner | −8.9% | 0.57 | 1.32 |
| (C16–C18) alkyldimethyl-siloxysilicate (MQ-G) | liquid | 2:1 | 50 cP | shampoo | +4.3% | 0.33 | 2.15 |
| poly(oxyethylene)dimethyl-siloxysilicate (MQ-H) | liquid | 2:1 | 340 cP | conditioner | −12.7% | 0.22 | 0.50 |

Note that in Table IX the resin denominated as "MQ-A" gave improved volume without significant adhesive character (Table VIII). In contrast to this performance, none of the MQ resins having an M:Q ratio of 2 were observed to provide significant volume; these resins had little or no adhesive character (Table VIII) and provided no volume despite the fact that they were deposited in quantities (relative values) comparable to or greater than the preferred trimethylsiloxysilicate (MQ-A) resin which also was observed to have no significant adhesive character. The MQ-B resin did provide significant volume but, unlike the MQ-A resin, exhibited adhesive character. Because of its adhesive character the MQ-B resin is expected to suffer from the same deficiencies as conventional fixative polymers.

Examples 16 and 17

Examples 16 and 17 were made using for each example: 16.80% ammonium lauryl sulfate; 0.30 sodium phosphate monobasic; 0.25% Polyquaternium-10; 2.00% cocodiethaa separate vessel the cocadiethanolamide, guar gum and distearyldimonium chloride were combined and heated to 50 degrees C with mixing. This was added to the main vessel with mixing. In a separate contained the distearyl phthalic acid amide was melted at 45–50 degrees C and then added to the vessel with mixing. The silicone MQ resin was added to the vessel and mixed for 15 minutes. The dimethicone was added to the vessel and mixed for 15 minutes. The vessel was then allowed to begin cooling. When the temperature of the mixture reached 40 degrees C, the fragrance was added. After continued cooling, the preservative was added below 38 degrees C. The final formulation was cooled to room temperature.

What is claimed is:

1. A volumizing shampoo comprising from 85–99.99 weight % of a hair care carrier which is a shampoo and from 0.01–15 weight % of an MQ resin of Formula IA:

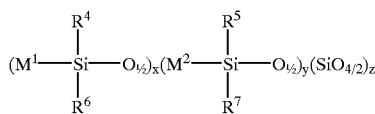

Formula IA wherein:

$M^1$ and $M^2$ are each independently from the group consisting of
(a) hydrogen,
(b) phenyl,
(c) phenethyl,
(d) a polyether of Formula II:

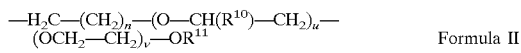

Formula II where n is a number from 1–20 and the —(CH$_2$)— chain may optionally contain 1or 2 unsaturations; u and v are integers each independently selected from 0–20, provided that u+v≧1; $R^{10}$ is selected from C1–C20 alkyl; and $R^{11}$ is selected from the group consisting of H, —CH$_3$ and —C(O)CH$_3$); and
(e) C1–C24 branched and unbranched hydrocarbons optionally substituted by a halogen substituted C1–C3 hydrocarbon radical; and wherein (1) (x+y)/z is a number in the range of 0.5 and 1.5, and (2) the values for $R^4$, $R^5$, $R^6$, $R^7$, x, y, z, $M^1$ and $M^2$ are selected to so that the MQ resin is a liquid having a viscosity of $1.0 \times 10^3 – 1 \times 10^6$ centipoise.

2. A composition according to claim 1 wherein the viscosity of the MQ resin is in the range of $1.5 \times 10^3 – 1 \times 10^6$ centipoise.

3. A composition according to claim 1 wherein the viscosity of the MQ resin is in the range of 1000–100,000 centipoise.

4. A composition according to claim 1 wherein the viscosity of the MQ resin is in the range of 1,000–50,000 centipoise.

5. A composition according to claim 1 wherein the MQ resin has a Formula IB:

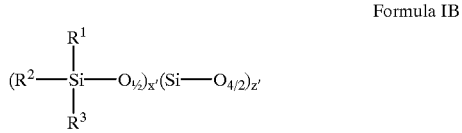

Formula IB where $R^2$ is selected from the same group as $M^1$; $R^1$ and $R^3$ are each independently selected from the same group as defined for $R^4$; and x'/z' is a number in the range of 0.5–1.5.

6. A composition according to claim 1 wherein $M^1$ and $M^2$ are each independently selected from the group consisting of C1–C23 branched and unbranched alkyl.

7. A composition according to claim 6 wherein $M^1$, $M^2$, $R^4$, $R^5$, $R^6$, and $R^7$ are each methyl.

8. A composition according to claim 5 wherein $R^2$ is selected from the group consisting of C1–C23 branched and unbranched alkyl.

9. A composition according to claim 8 wherein $R^1$, $R^2$, and $R^3$ are each methyl.

10. A composition according to claim 1 wherein (x+y)/z=1.

11. A composition according to claim 5 wherein x'/z'=1.

12. A composition according to claim 9 wherein x'/z'=1.

13. A composition according to claim 1 which additionally comprises a fixative.

14. A composition according to claim 1 comprising 0.1–7.5 weight % of the MQ resin.

15. A composition according to claim 14 comprising 0.1–5.0 weight % of the MQ resin.

16. A composition according to claim 14 comprising 0.2–2.5 weight % of the MQ resin.

17. A composition according to claim 13 additionally comprising 0.1–2.0 weight % of a conditioning agent.

18. A composition according to claim 1 comprising 4.00–60.00 weight % of a detersive surfactant, selected from the group consisting of at least one anionic detergent selected from the group consisting of $C_8$–$C_{18}$ alkyl sulfates, $C_8$–$C_{18}$ alkyl ethenoxy ether sulfates containing 1–5 ethenoxy groups in the molecule, $C_{10}$–$C_{18}$ acyl isethionates, $C_{10}$–$C_{20}$ alkyl sulfonates, $C_{10}$–$C_{20}$ alkylene sulfonates, and mixtures thereof; and optionally at least one of:

(i) 0.10–5.00 percent of an anionic hydrotropic, $C_1$–$C_3$ alkyl benzene sulfonate or $C_5$–$C_6$ alkyl sulfate;

(ii) 0.10–15.00 percent of an amphoteric surfactant selected from the group consisting of $C_8$–$C_{18}$ alkyl betaines, $C_8$–$C_{18}$ alkyl sulfobetaines, $C_8$–$C_{18}$ alkylamido $C_2$–$C_3$ alkyl betaines, $C_8$–$C_{18}$ alkylamido $C_2$–$C_3$ alkyl sulfobetaines, $C_8$–$C_{18}$ alkyl amphoacetates, $C_8$–$C_{18}$ alkyl amphopropionates, cocamidopropyl betaine, and mixtures thereof; and (iii) 0.1–4.0 percent of a nonionic surfactant, provided that the total amount of detersive surfactant does not exceed 60 percent by weight of the total weight of the composition.

19. A composition according to claim 1 additionally comprising 0.10–5.00 weight percent of a stabilizing agent.

20. A composition according to claim 1 wherein the viscosity of the MQ resin is in the range of 4,500–12,000 centipoise.

* * * * *